United States Patent [19]
Kaminsky et al.

[11] 3,937,828
[45] Feb. 10, 1976

[54] SUBSTITUTED PYRANO[3,2-C]
[1,2]BENZOTHIAZINE 6,6-DIOXIDES

[75] Inventors: Daniel Kaminsky, Parsippany;
Sylvester Klutchko, Hackettstown;
Maximilian von Strandtmann,
Rockaway, all of N.J.

[73] Assignee: Warner-Lambert Company, Morris Plains, N.J.

[22] Filed: July 31, 1974

[21] Appl. No.: 493,292

Related U.S. Application Data

[62] Division of Ser. No. 365,399, May 29, 1973.

[52] U.S. Cl. ................................. 424/246
[51] Int. Cl.² .......................... A61K 31/54
[58] Field of Search ...................... 424/246

[56] References Cited
UNITED STATES PATENTS
3,408,347   10/1968   Shavel et al. .................. 260/243

*Primary Examiner*—Norman A. Drezin
*Attorney, Agent, or Firm*—Albert H. Graddis; Frank S. Chow; Anne M. Kelly

[57] ABSTRACT

Novel pyrano[3,2-c][1,2]benzothiazine 6,6-dioxides are disclosed, substituted on the 3 position by a lower alkyl, carboxaldehyde, or hydroxymethyl group and, optionally substituted on the 5 position by a lower alkyl group. The corresponding aldehyde thiosemicarbazone derivatives of these compounds are also disclosed. Pharmaceutical compositions containing the substituted pyrano[3,2-c][1,2]benzothiazine 6,6-dioxides of this invention are useful in the treatment of hyperacidity; certain of these compounds also demonstrate anti-allergy activity.

2 Claims, No Drawings

SUBSTITUTED PYRANO(3,2-C) (1,2)BENZOTHIAZINE 6,6-DIOXIDES

This is a division of application Ser. No. 365,399 filed May 29, 1973.

SUMMARY OF THE INVENTION

This invention relates to novel pyrano[3,2-c][1,2]benzothiazine 6,6-dioxides having the formula I:

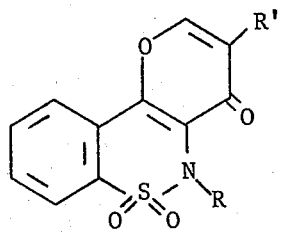

wherein R represents hydrogen and lower alkyl and R' represents lower alkyl, formyl and hydroxymethyl and the corresponding aldehyde thiosemicarbazone derivatives thereof. These compounds, and pharmaceutical compositions containing them, have anti-secretory activity and are useful in the treatment of hyperacidity; certain of these compounds demonstrate anti-allergy activity.

DETAILED DESCRIPTION OF THE INVENTION

The novel compounds of this invention have the general formula I:

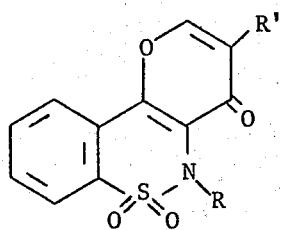

wherein R represents hydrogen and lower alkyl and R' represents lower alkyl, formyl and hydroxymethyl and the corresponding aldehyde thiosemicarbazone derivatives thereof.

Compounds having formula I wherein R and R' are as described above exhibit anti-secretory effects and can be used in relieving gastric hyperacidity. When administered to mammals, such as rats and guinea pigs in a suitable vehicle, as described below, they inhibit the gastric secretion of hydrochloric acid; acidity in the stomach is thus reduced. Pharmaceutical compositions containing compounds of formula I are indicated in the management of gastric hyperacidity and in the treatment of peptic ulcer resulting from such hyperacidity.

Compounds of formula I, when tested according to the procedure of H. Shay, Gastroenterology 5: p. 43 (1945) are effective in reducing gastric acidity in the pylorus ligated rat, when administered intraperitoneally at a dosage of 5 to 20 mg/kg of body weight. At a dosage of 5 to 40 mg/kg of body weight, administered intraduodenally, the same compounds are effective in reducing gastric acidity when subjected to this last mentioned test. Thus, the effective dose range for treatment of gastric hyperacidity is from 5 to 40 mg/kg of body weight of the mammal being treated, administered parenterally. Pharmaceutical compositions containing compounds having formula I may be administered in an aqueous gum tragacanth suspension as an intramuscular injection. The dosage regimen of from 5 to 40 mg/kg of body weight may be varied depending upon the severity of the condition and the weight, age and sex of the mammal being treated. As a particularly active class of compounds having anti-secretory activity, there may be mentioned those having formula I above, wherein R represents lower alkyl, preferably methyl, ethyl and butyl; and R' represents lower alkyl (preferably methyl), formyl and hydroxymethyl and the corresponding aldehyde thiosemicarbazone derivatives thereof.

Compounds of formula I wherein R represents lower alkyl, preferably methyl, ethyl and butyl, and R' represents formyl and hydroxymethyl have also been found to be useful in the treatment of allergic conditions. These compounds have been found to reduce responses to antigen challenge by inhibiting antibody and antigen reactions in mammals when tested in accordance with the procedure of I.Mota, Life Sciences, 4: No. 7, p. 465–474 (1963) and Ovary, Z. et al., Proc. Soc. Exptl. Biol. Med. 81: p. 584–586 (1952). The compounds may be administered to mammals such as rats or guinea pigs, parenterally or orally, at dosages of approximately 100 mg/kg of body weight.

Aforementioned compounds having anti-allergic properties may be administered in a parenterally acceptable vehicle such as a gum tragacanth suspension or they may be combined with pharmaceutical diluents such as lactose, cornstarch and the like and formulated into tablet or capsule dosage forms.

Pharmaceutical compositions containing aforementioned compounds having anti-allergic properties are useful in the management of allergic conditions such as bronchial asthma. To treat bronchial asthma, a dose of 100 mg/kg of body weight administered orally or parenterally is suggested. This dosage may be varied depending on the condition of the patient.

The novel compounds of this invention having formula I above may be prepared by either of the following procedures.

According to one process, described in co-pending application Ser. No. 365,398, filed May 29, 1973, compounds of formula I:

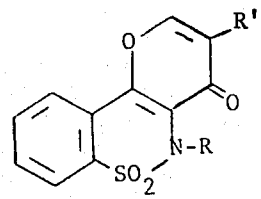

wherein R represents hydrogen and lower alkyl; R' represents lower alkyl and formyl, are prepared by reacting a starting material of the formula II or III:

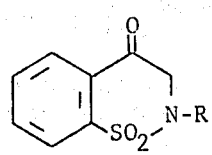

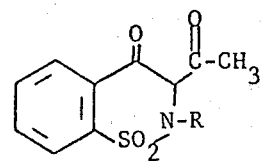

wherein R represents hydrogen and lower alkyl, with a boron trifluoride compound (preferably boron trifluoride etherate) and, in the case of starting material II, with an acid anhydride of the formula IV:

(R'CH$_2$CO)$_2$O  IV wherein R' represents hydrogen or lower alkyl, to obtain a boron complex intermediate having the formula V:

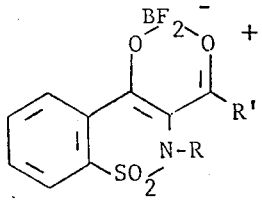

V wherein R represents hydrogen, lower alkyl and lower acyl and R' represents lower alkyl; and treating intermediate V with a Vilsmeier reagent (phosphorus oxychloride together with dimethylformamide), followed by hydrolysis.

The Vilsmeier reagent used is phosphorus oxychloride (POCl$_3$) with dimethylformamide (DMF). The substituents obtained on final compound I depend on the boron intermediate V used. For example, if R' in the boron intermediate V is methyl (i.e., the substituent in the 4-position is methyl) and DMF is used, a final compound I is obtained wherein R' is 3-formyl, as in Examples VII to X. However, when R' in the boron intermediate V is ethyl and DMF is used, a final compound I is obtained wherein R' is 3-methyl, as in Example XI.

Another unusual result occurs during the preparation of the compounds of this invention when 3-acetyl-2H-1,2-benzothiazin-4(3H)-one 1,1-dioxide is used as the starting material III in the process of aforementioned co-pending application Serial No. 365,398, filed May 29, 1973: an acetyl group attaches to the nitrogen atom of the boron intermediate complex, i.e., 5-acetyl-2,2-difluoro-4-methyl-2H-1,3,2-dioxaborino[5,4-c]1,2-benzothiazine 6,6-dioxide is formed (see Example IV). During the second step of the reaction, this 5-acetyl group is removed and the nitrogen atom in the final compound is unsubstituted.

The starting materials II and III above are prepared by known methods or obvious adaptations thereof, as described in Zinnes, H. et al., "1,2-Benzothiazines. II. The Preparation and Sodium Borohydride Reduction of 3-Acyl-2H-1,2-benzothiazin-4(3H)-one 1,1-Dioxides", *J. Org. Chem* 30: 2241-2246 (1965) and in Zinnes, H. et al., "1,2-Benzothiazines. III. The Preparation of 2H-1,2-Benzothiazin-4(3H)-one 1,1-Dioxide by the Acid-Catalyzed Deacetylation of β-Diketone", *J. Org. Chem* 31: 162-165 (1966).

The boron trifluoride compound used is, preferably, boron trifluoride etherate.

According to a second method, certain compounds of the subject invention having formula I:

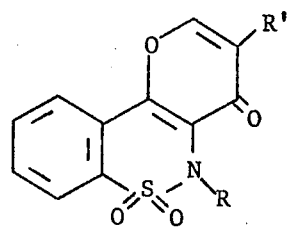

wherein R represents hydrogen and lower alkyl and R' represents hydroxymethyl may be prepared by treating the corresponding 4-hydroxy-2-lower alkyl-2H-1,2-benzothiazin-3-yl(methylsulfinyl)-methyl ketone S,S-dioxide having formula VI below:

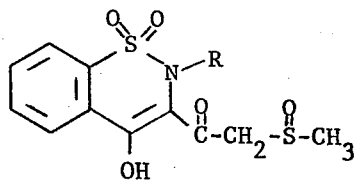

VI wherein R is as defined above, with formaldehyde to obtain intermediate VII below:

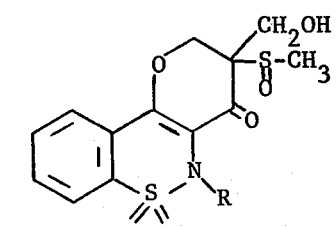

VII wherein R is as defined above, and thermally treating intermediate VII to eliminate CH$_3$SOH. Starting material VI and its preparation are generally described in co-pending U.S. Ser. No. 174,947, filed Aug. 25, 1971, now U.S. Pat. No. 3,806,644. The reaction procedure for converting starting material VI into the corresponding hydroxymethyl final compounds is generally described in co-pending application U.S. Ser. No. 309,329, filed Nov. 24, 1972, now U.S. Pat. No. 3,798,240.

In formulas I to VII above, the terms used to describe substitutents are more fully defined as follows: "lower alkyl" is meant to include lower aliphatic hydrocarbons having 1 to 6 (preferably 1 to 4) carbon atoms in the carbon chain such as methyl, ethyl, propyl, isopropyl, butyl, and isobutyl. The acyl in the term "lower acyl" is meant to include lower alkyl carboxylic acids wherein the "lower alkyl" moiety has the above described meaning.

In order to further illustrate the practice of this invention, the following examples are included:

EXAMPLE I

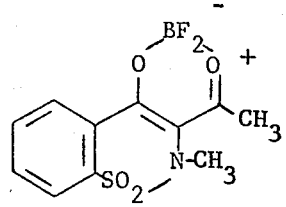

Preparation of 2,2-difluoro-4,5-dimethyl-2H-1,3,2-dioxaborino-[5,4-c][1,2]benzothiazine 6,6-Dioxide (Procedure A)

Seventy-one grams (0.5 mole) of boron trifluoride etherate is added to 42.3 g. (0.2 mole) of 2-methyl-2H-1,2-benzothiazin-4(3H)-one 1,1-dioxide* in 102 g. (1.0 mole) of acetic anhydride. The mixture is heated for 4 hrs. on a steam bath and then refluxed for 1 hr. The mixture is cooled, diluted with 250 ml. of ether, stirred and filtered to yield lt. brown solid complex; mp 163°–172°C. [Dry weight = 58.7 g. (97%)]. The analytical sample is obtained by recrystallization from ethyl acetate: Skellysolve C; mp. 213°–214°C.

Anal. Calcd for $C_{11}H_{10}BF_2NO_4S$: C, 43.88; H, 3.35; H, 4.65; S, 10.65. Found: C, 44.16; H, 3.43; N, 4.55; S, 10.75.

*Prepared by the method of H. Zinnes, R. A. Comes and J. Shavel, Jr., J. Org. Chem., 31, 162 (1966).

EXAMPLE II

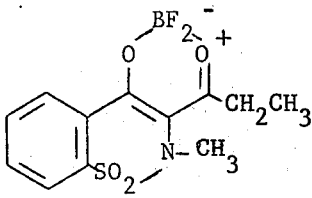

Preparation of 4-ethyl-2,2-difluoro-5-methyl-2H-1,3,2-dioxaborino-[5,4-c]1,2-benzothiazine 6,6-Dioxide (Procedure A)

Starting with 2-methyl-2H-1,2-benzothiazin-4(3H)-one 1,1-dioxide* and following the procedure A of Example I, but substituting propionic anhydride for acetic anhydride, 4-ethyl-2,2-difluoro-5-methyl-2H-1,3,2-dioxaborino[5,4-c]1,2-benzothiazine 6,6-dioxide is obtained having an mp of 134°–136°C.

Anal. Calcd: $C_{12}H_{12}BF_2NO_4S$: C, 45.74; H, 3.84; N, 4.45; F, 12.06. Found: C, 45.62; H, 3.94; N, 4.19; F, 12.17.

*Prepared by the method of H. Zinnes, R. A. Comes and J. Shavel, Jr., J. Org. Chem., 31, 162 (1966).

EXAMPLE III

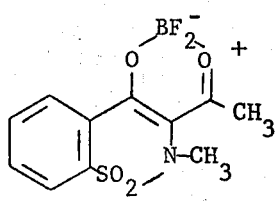

Preparation of 2,2-difluoro-4,5-dimethyl-2H-1,3,2-dioxaborino-[5,4-c]-1,2-benzothiazine 6,6-Dioxide (Procedure B)

Boron trifluoride etherate (142 g., 1.0 mole) is added to a mixture of 101 g. (0.4 mole) of 3-acetyl-2-methyl-2H-1,2-benzothiazin-4(3H)-one 1,1-dioxide* and 100 ml. of Ac₂O. This mixture is heated on a steam bath (permitting volatiles to escape) for 2 hours, then refluxed for 1 hr. After standing overnight, the mixture is diluted with about 500 ml. Et₂O, cooled, scratched and filtered. The crude lt. brown crystals are washed several times with ether and dried to yield 76.5% of material melting at 174°–183°C. The analytical sample from EtOAc: Skelly C melted at 213°–214°C. and is identical to the material prepared by Example I.

*Prepared by method of H. Zinnes, R. A. Comes, F. R. Zuleski, A. N. Caro and J. Shavel, Jr., J. Org. Chem., 30, 2241 (1965).

EXAMPLE IV

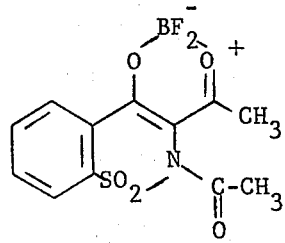

Preparation of 5-acetyl-2,2-difluoro-4-methyl-2H-1,3,2-dioxaborino-[5,4-c]1,2-benzothiazine 6,6-Dioxide (Procedure B)

Starting with 3-acetyl-2H-1,2-benzothiazin-4(3H)-one 1,1-dioxide* and following procedure B of Example III, 5-acetyl-2,2-difluoro-4-methyl-2H-1,3,2-dioxaborino[5,4-c]1,2-benzothiazine 6,6-Dioxide is obtained having an mp of 195°–197°C.

Anal. Calcd: $C_{12}H_{10}BF_2NO_5S$: C, 43.80; H, 3.06; S, 9.74. Found: C, 44.13; H, 3.08; S, 9.85.

*Prepared by the method of H. Zinnes, R. A. Comes and J. Shavel, Jr., J. Org. Chem., 31: 162 (1966)

EXAMPLE V

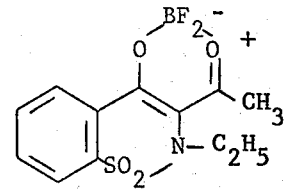

Preparation of 5-ethyl-2,2-difluoro-4-methyl-2H-1,3,2-dioxaborino-[5,4-c]1,2-benzothiazine 6,6-Dioxide (Procedure B)

Starting with 3-acetyl-2-ethyl-2H-1,2-benzothiazin-4(3H)-one 1,1-dioxide and following the procedure B of Example III, 5-ethyl-2,2-difluoro-4-methyl-2H-1,3,2-dioxaborino[5,4-c]1,2-benzothiazine 6,6-Dioxide is obtained having an mp of 167°–169°C.

Anal. Calcd.: $C_{12}H_{12}BF_2NO_4S$: C, 45.74; H, 3.84; S, 10.18. Found: C, 45.50; H, 3.87; S, 10.39.

EXAMPLE VI

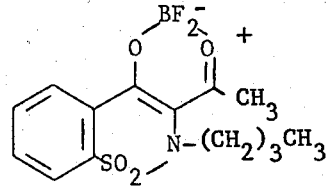

Preparation of 5-n-butyl-4-methyl-2H-1,3,2-dioxaborino[5,4-c]1,2-benzothiazine 6,6-Dioxide (Procedure B)

Starting with 3-acetyl-2-n-butyl-2H-1,2-benzothiazin-4(3H)-one 1,1-dioxide and following the procedure B of Example III, 5-n-butyl-4-methyl-2H-1,3,2-dioxaborino[5,4-c]1,2-benzothiazine 6,6-dioxide is obtained having an mp of 100°–102°C.

Anal. Calcd: $C_{14}H_{16}BF_2NO_4S$: C, 49.00; H, 4.73; S, 9.34. Found: C, 49.16; H, 4.73; S, 9.41.

EXAMPLE VII

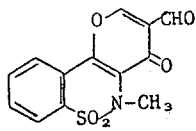

Preparation of 5-methyl-4-oxo-4H,5H-pyrano[3,2-c][1,2]benzothiazine-3-carboxaldehyde 6,6-Dioxide (Procedure C)

A solution of reagent is prepared by the slow addition of 153 g. (1.0 mole) of phosphorus oxychloride to ice cold DMF (365 g., 5 moles). The temperature is maintained below 10°C by use of a cooling bath. After stirring for an additional half-hour, 150 g. (0.5 mole) of 2,2-difluoro-4,5-dimethyl-2H-1,3,2-dioxaborino[5,4-c]-1,2-benzothiazine 6,6-dioxide is added and the reaction mixture is stirred for 15 minutes. The mixture is heated for 2 hours on a steam bath and poured over 2500 ml. ice water. After standing overnight, the mixture is filtered to yield 1t. brown solid product; mp 246°–254°C. Dry weight equals 131.6 g. (90% yield). The analytical material, recrystallized from DMF, melted at 258°–259°C (dec).

Anal. calcd for $C_{13}H_9NO_5S$: C, 53.61; H, 3.11; N, 4.81; S. 11.01. Found: C, 53.33; H 3.09; N, 4.90; S, 10.83.

EXAMPLE VIII

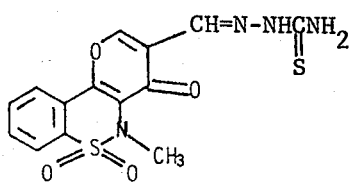

Preparation of 5-methyl-4-oxo-4H,5H-pyrano[3,2-c][1,2]benzothiazine-3-carboxaldehyde 3-thiosemicarbazone 6,6-dioxide hemihydrate The product of Example VII is reacted with thiosemicarbazide in dioxane to obtain 5-methyl-4-oxo-4H,5H-pyrano[3,2-c][1,2]-benzothiazine-3-carboxaldehyde 3-thiosemicarbazone 6,6-dioxide hemihydrate having an mp of 227°–229°C (dec).

Anal. Calcd: $C_{14}H_{12}N_4S_2O_{4.1/2}H_2O$: C, 45.03; H, 3.51; N. 15.00; S, 17.17. Found: C, 45.13; H, 3.49; M, 14.91; S, 16.85.

EXAMPLE IX

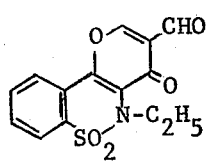

Preparation of 5-ethyl-4-oxo-4H,5H-pyrano[3,2-c][1,2]benzothiazine-3-carboxaldehyde 6,6-dioxide (Procedure C)

Starting with 5-ethyl-2,2-difluoro-4-methyl-2H-1,3,2-dioxaborino[5,4-c]1,2-benzothiazine 6,6-dioxide from Example V and following procedure C of Example VII, 5-ethyl-4-oxo-4H,5H-pyrano[3,2-c][1,2]benzothiazine-3-carboxaldehyde 6,6-dioxide is obtained having an mp of 160°–162°C.

Anal. Calcd: $C_{14}H_{11}NO_5S$: C, 55.08; H, 3.63; N, 4.59. Found: C, 54.96; H, 3.56; N, 4.11.

EXAMPLE X

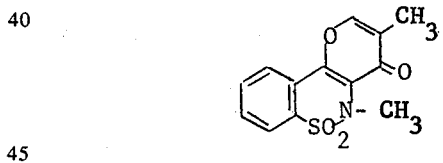

Preparation of 5-n-butyl-4-oxo-4H,5H-pyrano[3,2-c][1,2]benzothiazine-3-carboxaldehyde 6,6-dioxide (Procedure C)

Starting with 5-n-butyl-4-methyl-2H-1,3,2-dioxaborino[5,4-c]1,2-benzothiazine 6,6-dioxide from Example VI, and following procedure C of Example VII 5-n-butyl-4-oxo-4H,5H-pyrano[3,2-c][1,2]benzothiazine-3-carboxaldehyde 6,6-dioxide is obtained, having an mp of 108°–110°C.

Anal. Calcd.: $C_{16}H_{15}NO_5S$: C, 57.65; H, 4.54; N, 4.20. Found: C, 57.70; H, 4.58; N, 4.24.

EXAMPLE XI

Preparation of 3,5-Dimethylpyrano[3,2-c][1,2]benzothiazin-4(5H)-one 6,6-dioxide (Procedure C)

Starting with 4-ethyl-2,2-difluoro-5-methyl-2H-1,3,2-dioxaborino[5,4-c]-1,2-benzothiazine 6,6-dioxide from Example II and using procedure C of Example VII, the subject compound is obtained as an almost colorless crystalline product; mp 214°–216°C (from chloroform: Skellysolve C).

Anal. Calcd: $C_{13}H_{11}NO_4S$: C, 56.31; H, 4.00; N, 5.05. Found: C, 56.20; H, 3.97; N, 5.07.

EXAMPLE XII

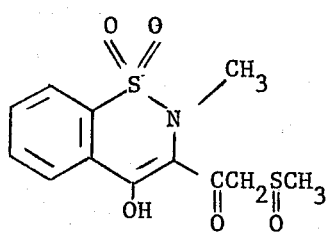

Preparation of 4-hydroxy-2-methyl-2H-1,2-benzothiazin-3-yl (methylsulfinyl)methyl ketone S,S-dioxide This was prepared by reacting 64.8 g of ethyl 4-hydroxy-2-methyl 2H-1,2-benzothiazin-3-carboxylate 1,1-dioxide* with 35 g of NaH (57% suspension in mineral oil) in a mixture of 960 ml of benzene and 480 ml of DMSO. A mixture of 480 ml of DMSO, 960 ml of benzene and 35 g of NaH (57% suspension in mineral oil) is heated, with stirring, under a stream of nitrogen for one and one-half hours at 75°C. on a water bath. The clear solution that formed was cooled to 25°C. on an ice bath. The bath was removed and 64.8 g of ethyl 4-hydroxy-2-methyl-2H-1,2-benzothiazin-3-carboxylate 1,1-dioxide was added. The temperature rose to 38°C. The reaction mixture was stirred for one and one-half hours and diluted to a 5 liter volume with anhydrous ether. A heavy gum precipitated. The supernatant liquid was decanted. The gum was washed with anhydrous ether several times and then dissolved in 400 ml of water. The aqueous solution was adjusted to pH 6 in the cold with glacial acetic acid. All that precipitated was extracted with methylene chloride (five 100 ml portions). The combined methylene chloride extracts were dried over sodium sulfate and taken down to a solid under reduced pressure. The salt was recrystallized from $CH_3CN$, mp 160°–161°C. Yield 47 g (62% of theory).

Anal. Calcd: $C_{12}H_{13}NO_5S_2$: C, 45.70; H, 4.16; N, 4.44; S, 20.33. Found: C, 45.79; H, 3.97; N, 4.29; S, 20.05.

*Prepared as in U.S. Pat. No. 3,501,466

EXAMPLE XIII

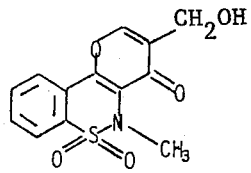

Preparation of 3-(hydroxymethyl)-5-methylpyrano[3,2-c][1,2]benzothiazin-4(5H)-one 6,6-dioxide (Procedure D)

A solution of 4.0 g (0.0127 mole) of 4-hydroxy-2-methyl-2H-1,2-benzothiazin-3-yl(methylsulfinyl)methyl ketone S,S-dioxide (prepared in Example XII), 500 ml of methanol, 6.3 g (0.078 mole) of 37% formaldehyde and 15 drops of piperidine is maintained at reflux for 1 hour, concentrated to remove the methanol, diluted with 200 ml of toluene and heated to 100°C. The toluene solution is decanted from a small amount of undissolved material and heated at the boiling point for one-half hour, allowing about half of the volume to distill off. The cooled solution is decanted from some separated red oil. The crystals that separate on standing are filtered; weight 0.9 g (24.2%); mp 201°–205°C. Recrystallization from methanol gives pure product; mp 213°–215°C.

Anal. Calcd: $C_{13}H_{11}NO_5$: C, 53.24; H, 3.78; N, 4.78. Found: C, 53.06; H, 3.66; N, 4.58.

We claim:

1. A method for preventing asthmatic symptoms which comprises administering to a mammal in need thereof an effective amount of a compound of the formula:

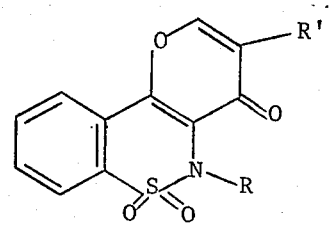

wherein R represents lower alkyl; and R' represents carboxaldehyde and hydroxymethyl.

2. A method according to claim 1 wherein 100 mg/kg of body weight of the compound is administered to a mammal.

* * * * *